United States Patent
Ruton et al.

(10) Patent No.: US 6,409,676 B2
(45) Date of Patent: *Jun. 25, 2002

(54) PROCESS FOR DETERMINING RESPIRATORY PHASES OF THE SLEEP OF A USER

(75) Inventors: Stéphane Ruton, Viroflay; Benoit Jonquet, Palaiseau, both of (FR)

(73) Assignee: Taema, Antony Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/732,873

(22) Filed: Dec. 11, 2000

Related U.S. Application Data

(62) Division of application No. 09/335,724, filed on Jun. 18, 1999, now Pat. No. 6,190,328.

(30) Foreign Application Priority Data

Jun. 18, 1998 (FR) ............................................. 98 07695

(51) Int. Cl.⁷ ................................................. A61B 5/08
(52) U.S. Cl. ....................................................... 600/532
(58) Field of Search .................................. 600/532, 533, 600/538, 529

(56) References Cited

U.S. PATENT DOCUMENTS 5,309,921 A    5/1994  Kisner et al.
5,522,382 A    6/1996  Sullivan et al.
5,772,599 A    6/1998  Nevo et al.
6,190,328 B1 * 2/2001  Ruton et al. ................ 600/532

FOREIGN PATENT DOCUMENTS

EP    0404427 A1    12/1990
GB    2214302 A      8/1989
WO    WO 9812965     4/1998

OTHER PUBLICATIONS

J.E. Daniels et al., "Cadosa: A Fuzzy Expert System for Differential Diagnosis of Obstructive Sleep Apnoea and Related Conditions," Expert Systems with Applications, vol. 12, 1997, pp. 163–177.

* cited by examiner

Primary Examiner—John P. Lacyk
(74) Attorney, Agent, or Firm—Young & Thompson

(57) ABSTRACT

A process for determining respiratory phases of the sleep of a user (3), comprising measuring at least two physical variables of which at least a first physical variable is representative of the nasal flow of the user (3) and of which at least a second physical variable is representative of the user's buccal flow. The process furthermore comprises processing and converting each physical variable with a view to establishing its degree of membership in at least one state of a fuzzy variable, and applying pre-established rules between at least one state of a first fuzzy variable and a state of a second fuzzy variable so as to evaluate the degree of membership in a respiratory phase state of the sleep of the user (3) according to fuzzy logic.

14 Claims, 4 Drawing Sheets

PROCESS FOR DETERMINING RESPIRATORY PHASES OF THE SLEEP OF A USER

This application is a division of application Ser. No. 09/335,724, filed on Jun. 18, 1999, now U.S. Pat. No. 6,190,328 the entire contents of which are hereby incorporated by reference.

FIELD OF THE INVENTION

The invention relates to a device and to a process for determining respiratory phases of the sleep of a user.

BACKGROUND OF THE INVENTION

Respiratory disorders of sleep, such as the Sleep Apnea Syndrome (SAS) are characterized, in general, by a disfunctioning of the respiratory function during sleep.

Considerable fragmentation of sleep is observed in subjects affected by such a syndrome, with short phases of sleep and the resumption of normal respiration usually accompanied by a brief period of wakefulness, lasting a few seconds.

The normal course of sleep, from the stage of light sleep to the stage of deep sleep, via a stage of paradoxical sleep, is greatly disturbed, this having consequences on the daytime routine of these subjects. Thus, they tend to be drowsy, or even to fall asleep when fully active, and a decrease in intellectual and sexual functions is also observed in them, together with the risks of hypertension and cardiac insufficiency.

Respiratory disorders may be of the obstructive or central type.

In the first case, a total obstruction (obstructive apnea) or partial obstruction (obstructive hypopnea) of the upper airways is observed while muscular effort is maintained. Disorders of this type are often associated with considerable snoring.

In the second case, muscle control is absent (central apnea) or diminished (central hypopneal), the upper airways being open.

Obstructive disorders represent the great majority of nocturnal respiratory disorders.

Customarily, diagnosis of respiratory sleep disorders is performed in a sleep laboratory by recording and studying numerous parameters related:

either to sleep; electroencephalogram, electroocculogram, electromyogram, or to cardio-respiratory function: electrocardiogram, respiratory frequency, nasal and/or buccal flow, thoracic and abdominal movements, arterial oxygen saturation, snoring.

Diagnosis of these sleep pathologies is recent and its implementation is unwieldy and requires that the subject be hospitalized for one or two nights.

The treatment of respiratory sleep disorders customarily employs an appliance for keeping the upper airways open.

This appliance usually comprises a mask-based positive pressure apparatus (CPAP), in which a means of compressing the ambient air, operated by a control device, delivers air pressure to a pipe and then to a mask placed on the patient's nose in a leaktight manner.

The control device compares the value of the pressure in the mask with a set pressure target value and, depending on the deviation measured, adjusts a control signal which it delivers to the means for compressing the ambient air.

At present, the pressure target value to be applied in the mask of the patient is determined empirically in the sleep laboratory by progressively increasing an initial target value and observing the consequences for the respiratory disorders, the value chosen being the first value for which normal unfragmented sleep is observed.

There are apparatuses for diagnosing or/and treating these nocturnal respiratory disorders, which detect apneas or hypopneas, but do not differentiate between central and obstructive events.

Others, after having detected an apnea, send a pressure pulse to the patient's mask and study any echo: if there is no echo, the event is central, and if an echo returns, the event is obstructive.

Such apparatuses are described in particular in the documents FR-A-2663547 and FR-A-2674133.

However, in order to be able to establish a correct diagnosis of respiratory disorders (apneas, hypopneas, pathology of increased resistance, etc.) and/or to determine and/or initiate adequate and effective treatment, it may be necessary or even vital for the practitioner, that is to say the doctor or the like, to have a reliable image representative of the succession of the various inhalatory and exhalatory phases of his patient, that is to say the image of the subject's respiratory flow or rate of flow.

However, existing processes and apparatuses do not allow this kind of reliable and accurate determination of the image of the said respiratory rate of flow.

Henceforth, it is readily understood that diagnosis and/or subsequent treatment may be incorrect or incomplete.

SUMMER OF THE INVENTION

The aims of the present invention are therefore to propose a process and an apparatus for diagnosing and/or treating respiratory sleep disorders:

which are able to allow the reliable and accurate determination, from various respiration parameters for a patient, of the latter's various respiratory phases, which are able to determine accurately the phases of snoring and/or phenomena with a partial obstruction of the patient's respiratory passages, which can be used both in a sleep laboratory, that is to say in a hospital environment, and also at the patient's home, and which have a reasonable cost.

To this end, the subject of the invention is a device for determining respiratory phases of the sleep of a user, comprising means for measuring at least two physical variables of which at least a first physical variable is representative of the nasal flow of the user and of which at least a second physical variable is representative of the user's buccal flow, characterized in that it furthermore comprises means for processing and converting each physical variable with a view to establishing its degree of membership in at least one state of a fuzzy variable, and means for applying pre-established rules between at least one state of a first fuzzy variable and a state of a second fuzzy variable so as to evaluate the degree of membership in a respiratory phase state of the sleep of the user according to fuzzy logic.

The device according to the invention can additionally comprise one or more of the following characteristics:

each fuzzy variable possesses at least two states, the states of respiratory phases of sleep comprise at least one state of normal respiration, a state of apnea and a state of hypopnea, the degrees of membership of the states associated with a fuzzy variable are established on the basis of continuous curves defined over the entire universe of discourse of a measured physical variable, the measurement means comprise a pressure sensor linked to a nose piece intended to be worn by the user and one of the measured physical variables is the pressure signal measured by the said pressure sensor, the processing and conversion means comprise means for extracting from the measured pressure signal snoring phases associated with breathing-obstruction phenomena, the means for extracting snoring phases comprise means of high-pass filtering of the pressure signal, means for amplifying the filtered signal, means for interpolating the amplified filtered signal so as to obtain an envelope curve, means for storing a reference curve and means for comparing the envelope curve with the reference curve so as to determine the presence of snoring phases, the measurement means comprise a current sensor measuring the current consumed by a low-inertia turbine which is linked to the nose piece and one of the measured physical variables is the current consumed by the turbine, the processing and conversion means comprise means for extracting from the signal of current consumed an image of the nasal flow of the user, means for determining the phases of nasal inhalation and exhalation of the user, means for calculating the time derivative of the amplitude of the nasal flow during an inhalation phase and means for utilizing the derivative so as to determine whether the user is or is not suffering from a partial obstructive phenomenon, the means for utilizing the derivative of the amplitude of the nasal flow comprise means for comparing the absolute value of the derivative with at least one reference value and means for measuring the duration for which the absolute value of the derivative is less than the at least one reference value, the means for utilizing the derivative furthermore comprise means for charting the number of changes of sign of the derivative when the latter is less than the reference value, the measurement means comprise a member for measuring the resistance of a thermistor intended to be placed in proximity to the mouth of the user, and one of the measured physical variables is the resistance measured by the member for measuring the resistance of the thermistor.

The subject of the invention is also a process for determining respiratory phases of the sleep of a user, characterized in that it comprises the following steps:

at least two physical variables are measured, of which at least a first physical variable is representative of the nasal flow of the user and of which at least a second physical variable is representative of the user's buccal flow, each physical variable is processed and converted with a view to establishing its degree of membership in at least one state of a fuzzy variable, and pre-established rules between at least one state of a first fuzzy variable and a state of a second fuzzy variable are applied so as to evaluate the degree of membership in a respiratory phase state of the sleep of the user according to fuzzy logic.

This process can moreover comprise one or more of the following characteristics:

each fuzzy variable possesses at least two states, the states of respiratory phases of sleep comprise at least one state of normal respiration, a state of apnea and a state of hypopnea, the degrees of membership of the states associated with a fuzzy variable are established on the basis of continuous curves defined over the entire universe of discourse of a measured physical variable, one of the measured physical variables is the pressure in a nose piece worn by the user, during the processing and conversion, snoring phases associated with breathing-obstruction phenomena are extracted from the measured pressure signal, during extraction, high-pass filtering of the pressure signal is carried out, the filtered signal is amplified, the amplified filtered signal is interpolated so as to obtain an envelope curve, and the envelope curve is compared with a reference curve so as to determine the presence of snoring phases, to obtain an image of the nasal flow, the current consumed by a low-inertia turbine which is linked to the nose piece worn by the user is for example measured, during extraction of the image of the nasal flow, the phases of inhalation and exhalation of the user are determined and the time derivative of the amplitude of the nasal flow during an inhalation phase is calculated and this derivative thus calculated is utilized to determine whether or not the user is suffering from a partial obstructive phenomenon, during utilization of the derivative of the amplitude of the nasal flow, the absolute value of this derivative is compared with at least one reference value, and the duration for which the absolute value of the derivative is less than the said at least one reference value is measured, during utilization of the derivative of the amplitude of the nasal flow, the number of changes of sign of the derivative when the absolute value of the latter is less than the at least one reference value is moreover charted, to obtain an image of the buccal flow, the resistance of a thermistor placed in proximity to the said user's mouth is for example measured.

The subject of the invention is also a method for diagnosing the respiratory phases of the sleep of a patient suffering from respiratory sleep disorders, in particular sleep apnea, characterized in that it comprises the following steps:

at least two physical variables are measured, of which at least a first physical variable is representative of the nasal flow of the user and of which at least a second physical variable is representative of the user's buccal flow, each physical variable is processed and converted with a view to establishing its degree of membership in at least one state of a fuzzy variable, and pre-established rules between at least one state of a first fuzzy variable and a state of a second fuzzy variable are applied so as to evaluate the degree of membership in a respiratory phase state of the sleep of the user according to fuzzy logic.

This process can additionally comprise one or more of the following characteristics:

each fuzzy variable possesses at least two states, the states of respiratory phases of sleep comprise at least one state of normal respiration, a state of apnea and a state of hypopnea, the degrees of membership of the states associated with a fuzzy variable are established on the basis of continuous curves defined over the entire universe of discourse of a measured physical variable, one of the measured physical variables is the pressure in a nose piece worn by the user, during the processing and conversion, snoring phases associated with breathing-obstruction phenomena are extracted from the measured pressure signal, during extraction, high-pass filtering of the pressure signal is carried out, the filtered signal is amplified, the amplified filtered signal is interpolated so as to obtain an envelope curve, and the envelope curve is compared with a reference curve so as to determine the presence of snoring phases, to obtain an image of the nasal flow, the current consumed by a low-inertia turbine which is linked to the nose piece worn by the patient is for example measured, during extraction of the image of the nasal flow, the phases of inhalation and exhalation of the said patient are determined and the time derivative of the amplitude of the nasal flow during an inhalation phase is calculated and this derivative thus calculated is utilized to determine whether or not the patient is suffering from a partial obstructive phenomenon, during utilization of the derivative of the amplitude of the nasal flow, the absolute value of this derivative is compared with at least one reference value, and the duration for which the absolute value of the derivative is less than the at least one reference value is measured, during utilization of the derivative of the amplitude of the nasal flow, the number of changes of sign of the derivative when the absolute value of the latter is less than the at least one reference value is moreover charted, to obtain an image of the buccal flow, the resistance of a thermistor placed in proximity to the patient's mouth is for example, measured.

BRIEF DESCRIPTION OF DRAWINGS

Other characteristics and advantages of the invention will emerge from the following description given by way of example, without limiting character, with regard to the appended drawings in which.

1. STRUCTURE OF THE DEVICE ACCORDING TO THE INVENTION

Figure 1:
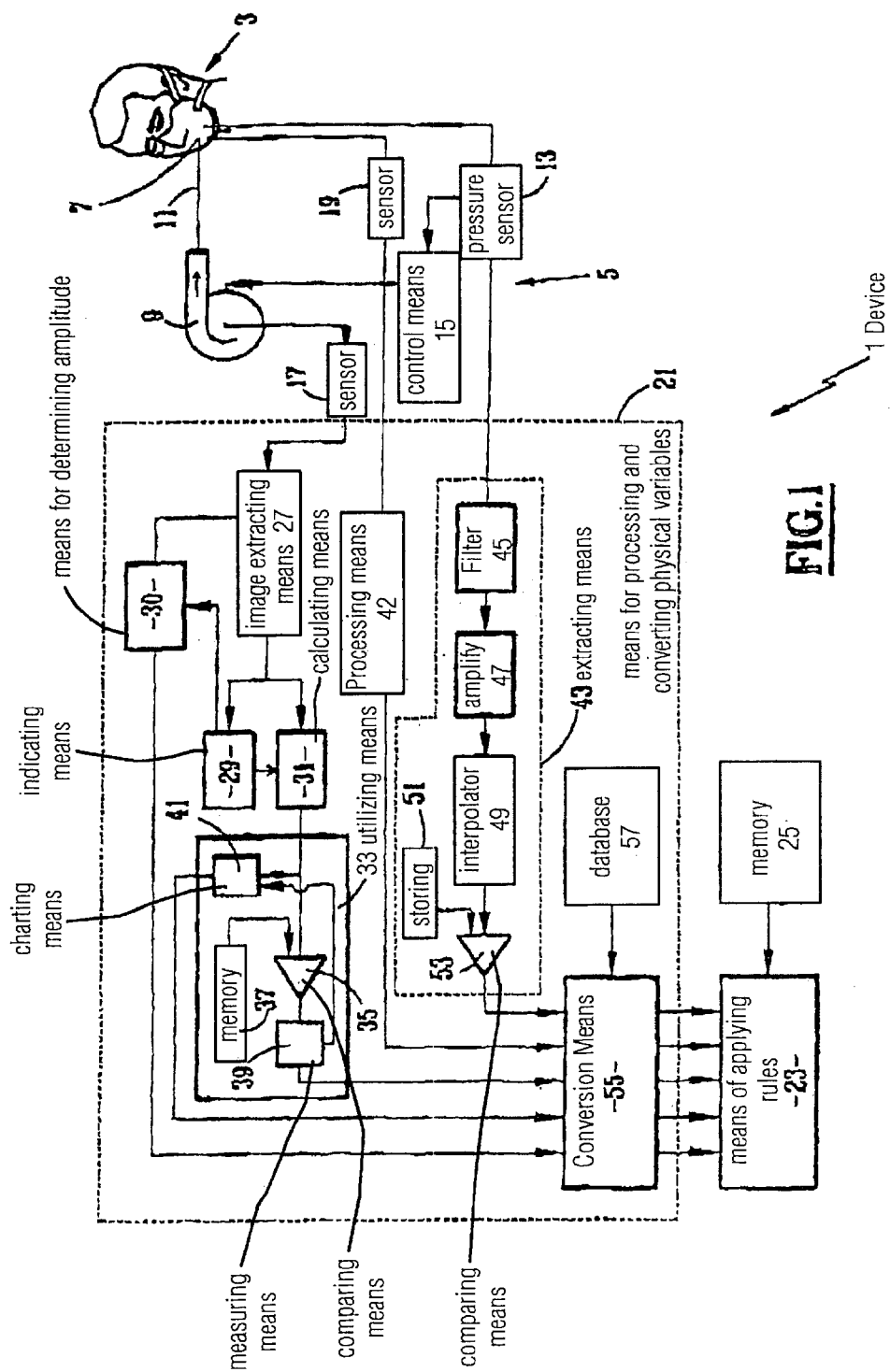
FIG. 1 is a schematic diagram of a device according to the invention.

Represented in FIG. 1 is a device 1 according to the invention making it possible to determine respiratory phases of the sleep of a user 3.

This device 1 comprises means 5 for measuring at least two physical variables, of which at least a first physical variable is representative of the nasal flow of the user and of which at least a second physical variable is representative of the user's buccal flow.

To this end, the user 3 wears a mouth- and/or nose-piece 7, such as a mask and/or breathing kit which are known per se and will not be described in detail here.

To this nose/mouth piece 7 is connected a low-inertia turbine 9 by means of a breathing pipe 11 making it possible to convey the pressurized breathing gas to the respiratory passages of the user 3.

As the case may be, the breathing gas is dispensed at a positive pressure which is constant over time, that is to say at a single pressure level (CPAP type apparatus), or at a pressure which varies between at least one low pressure level and at least one higher pressure level, that is to say at several pressure levels (BPAP type apparatus). The manner of operation of such apparatuses having already been described many times in the prior art, it will not be detailed hereinbelow. However, for further details, reference may be made in particular to the following documents: U.S. Pat. Nos. 5,492,113, 5,239,995, EP-A-0 656 216 or EP-A-0 505 232.

A pressure sensor 13 whose pressure tap point is arranged on the nose/mouth piece 7, that is to say in immediate proximity to the respiratory passages of the user 3, makes it possible to detect the pressure variations due to the breathing of the user. This sensor 13 is linked to means 15 controlling the turbine 9 so as to supply these means 15 with a pressure signal. On the basis of the pressure signal received and of a specified overpressure target value, these means 15 supply a control signal to the turbine 9 in such a way as to modulate the overpressure supplied by the turbine 9 to the user 3 (see also EP-A-505232 or U.S. Pat. No. 5,443,061).

Given that the pressure of the breathing gas supplied to the user must be almost constant, it is understood that the motor speed of the turbine 9 and therefore the amount of current consumed by the latter is dependent on the control signal of the means 15 and therefore corresponds to the nasal flow of the user 3.

This is why, to obtain an image of the nasal flow, a current sensor 17 measures the current consumed by the turbine 9.

Moreover, in order to supplement the image of the nasal flow with an image of the buccal flow, a sensor such as for example a thermistor (not visible in the figure) is placed in the mouth/nose piece in proximity to the mouth of the user 3.

This sensor, for example the abovementioned thermistor, is linked to a measurement member 19 measuring, in the case of a thermistor, the resistance of the latter.

In effect, the measurement value such as, for example, the resistance of the thermistor is modified by temperature variations caused by any buccal flow issuing from the mouth of the user 3, thereby making it possible to obtain an image of the buccal flow which is reliable and accurate.

To determine the respiratory phases of the sleep of the user 3 from the values of the physical variables measured by way of the sensors 13, 19 and 17, that is to say the images of the pressure, of the nasal flow and of the buccal flow, the device 1 furthermore comprises means 21 for processing and converting each physical variable charted with a view to establishing its degree of membership in at least one state of a fuzzy variable. The degrees of membership of the respective states of the fuzzy variables are input into means 23 for applying rules stored in a memory 25 forming a knowledge base.

The processing and conversion means 21 comprise means 27 for extracting from the signal of current consumed, measured by the current sensor 17, an image of the nasal flow of the user 3, that is to say the variation of the nasal flow over time. This image of the nasal flow of the user 3 is input into means 29 for determining the phases of nasal inhalation and exhalation of the user, into means 30 for determining the amplitude of the nasal flow and into means 31 for calculating the time derivative of the amplitude of the nasal flow.

The means 30 furthermore receive a control signal for the means 29 indicating which phase of respiration the user is in.

The means 31 only calculate the derivative of the nasal flow during an inhalation phase. This is why the means 29 also send a control signal to the means 31 for calculating the derivative when they have determined that the user is in a nasal inhalation phase.

The derivative calculated by the means 31 is input into utilizing means 33. These utilizing means 33 comprise means 35 for comparing the absolute value of the derivative with at least one reference value recorded in a memory 37. Depending on the result of the comparison, the means 35 activate means 39 for measuring the duration for which the absolute value of the derivative is less than the at least one reference value.

Moreover, the means 33 comprise, linked to the means 31 for calculating the derivative as well as to the comparison means 35, means 41 for charting the number of changes of sign of the derivative when the absolute value of the latter is less than the reference value.

The means 33 for utilizing the derivative of the amplitude of the nasal flow are employed to determine whether or not the user is suffering from a partial obstruction of the respiratory passages, as will be explained in detail hereinbelow.

The processing and conversion means 21 furthermore comprise means 42 for processing the signal delivered by the member 19 for measuring for example the resistance of the thermistor.

Additionally, the processing and conversion means 21 comprise means 43 for extracting from the pressure signal, measured by the pressure sensor 13, snoring phases associated with breathing-obstruction phenomena.

These extraction means 43 comprise means 45 of high-pass filtering of the pressure signal, means 47 for amplifying the filtered signal, means 49 for interpolating the amplified filtered signal so as to obtain an envelope curve, means 51 for storing a reference curve and means 53 for comparing the envelope curve with the reference curve so as to determine the presence of snoring phases.

The various physical variables thus processed are input into means 55 for converting each of these variables with view to establishing its degree of membership in at least one state of an associated fuzzy variable. This conversion, which will be explained in greater detail below, is carried out on the basis of continuous curves defined over the entire universe of discourse of the physical variables stored in a database 57 linked to the conversion means 55.

II. MANNER OF OPERATION OF THE DEVICE ACCORDING TO THE INVENTION

The manner of operation of the device 1 according to the invention will be explained hereinbelow while setting forth in detail on the one hand the various processing and conversion steps implemented in the processing and conversion means 21, and on the other hand the implementing of the application of the rules to the fuzzy variables by the means 23 according to fuzzy logic.

Figure 2:
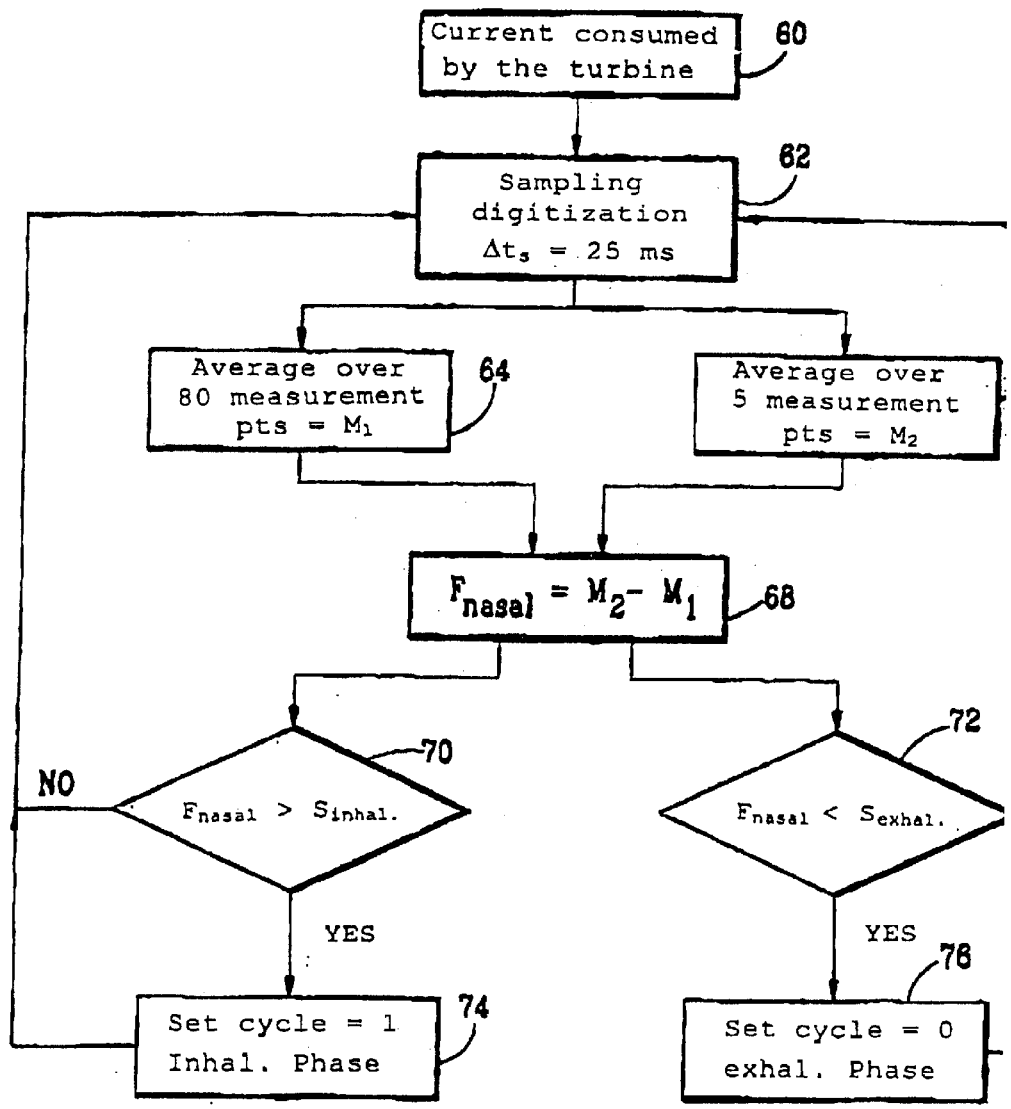
FIG. 2 is a flowchart showing certain steps in the processing of a physical variable representative of the nasal flow of a user.

II.1 Determination of the Phases of Nasal Inhalation and Exhalation of the User as well as of the Amplitude of the Nasal Flow Represented in FIG. 2 are the main operating steps implemented by the means 27 and 29.

During a first step 60, the signal of current consumed by the turbine 9, delivered by the current sensor 17, is input into the extraction means 27 and is then digitized there and sampled at a rate of $\Delta t_5 = 25$ ms during a second step 62.

Next, during a step 64, the average $M_1$ of eighty sampled values is calculated, this corresponding to an average of the measurement values over a duration of 20 seconds. This duration of 20 s corresponds to two or three breathing cycles of the user.

In parallel with this, during a step 66, the average $M_2$ of five sampled values is calculated, this corresponding to an average of the measurement values over a duration of 125 milliseconds and being in fact the almost raw signal, slightly smoothed.

During a next step 68, the nasal flow $F_{nasal}$ is calculated as the difference between $M_2$ and $M_1$.

Then, during steps 70 and 72, $F_{nasal}$ is compared with respective thresholds $S_{inhal}$ and $S_{exhal}$. The thresholds $S_{inhal}$ and $S_{exhal}$ correspond to values representative of the rate of flow of the nasal flow respectively above or below which it is almost certain that the user is in a phase of inhalation or exhalation. Of course $S_{inhal}$ is greater than $S_{exhal}$. The thresholds $S_{inhal}$ and $S_{exhal}$ can be determined empirically by clinical trials on users.

If, during step 70, $F_{nasal}$ is greater than the threshold $S_{inhal}$, the value one is allocated during a step 74 to a variable named cycle, cycle=1 therefore signifying that the user 3 is in a nasal inhalation phase, and then we return to step 62. If $F_{nasal}$ is less than the threshold value $S_{inhal}$, we return directly to step 62.

If, during the comparison step 72, $F_{nasal}$ is less than $S_{exhal}$, then the value zero is allocated during step 76 to the variable cycle, cycle=0 signifying that the user 3 is in a nasal exhalation phase, and then we return to step 62. If $F_{nasal}$ is greater than the threshold value $S_{exhal}$, we return directly to step 62.

Figure 3:
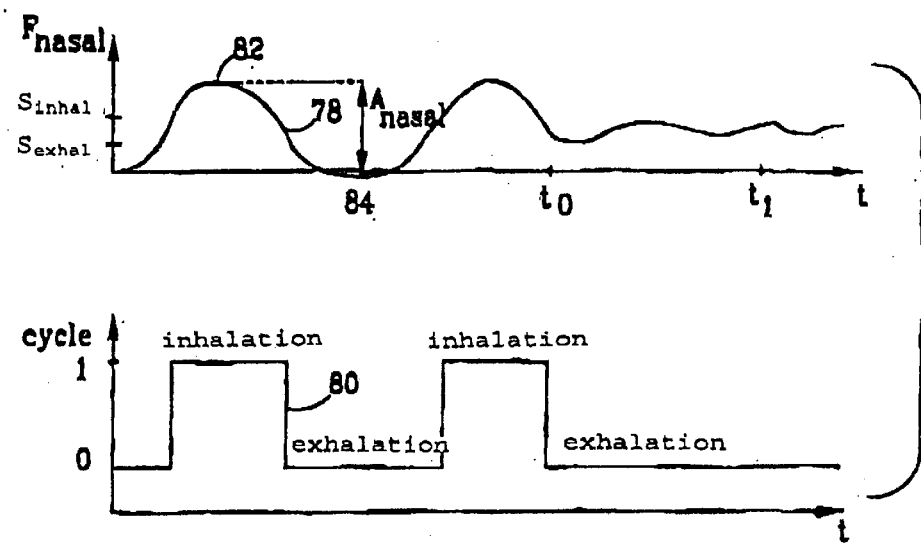
FIG. 3 shows two graphs to illustrate in particular the steps described with reference to FIG. 2.

These steps making it possible to determine the phases of nasal inhalation and exhalation of the user are illustrated in FIG. 3. This FIG. 3 shows two graphs of which one, the upper graph, shows a curve 78 of the nasal flow $F_{nasal}$ as a function of time and the other, the lower graph, shows a curve 80 of the values of the variable cycle which are allocated to this variable as a function of the value of the nasal flow $F_{nasal}$.

In this figure, it is clearly seen that as soon as $F_{nasal}$ exceeds the threshold $S_{inhal}$, cycle takes the value 1, and if $F_{nasal}$ is less than $S_{exhal}$, cycle takes the value 0. Up to the instant referenced $t_0$ it is possible to regard the user having a normal breathing cycle.

Beyond $t_0$, $F_{nasal}$ no longer manages, after entering an exhalation phase, to exceed $S_{inhal}$ and cycle remains at the value 0. This may be due to buccal respiration of the user, but also to sleep hypopnea or apnea.

Furthermore, by measuring the time between the start of two inhalation phases (cycle=1), the duration of the user's breathing cycles is determined. By measuring the duration of the exhalation phases, the potential ranges of sleep hypopnea and apnea are determined since these phenomena are regarded as occurring only for prolonged nasal exhalation phases, typically for exhalation phases having a duration of greater than 3 seconds. For example, in FIG. 3 the user is, onwards of the instant $t_0$, in a nasal exhalation phase. Onwards of the instant $t_1$, 3s later than $t_0$, the user is again in the nasal exhalation phase and therefore in a potential time range of sleep hypopnoea or apnoea.

Additionally, to calculate the amplitude of the nasal flow $A_{nasal}$ the means 30 determine, during an inhalation phase, the maximum of the nasal flow $F_{nasal}$ (bearing the reference number 82) and during an exhalation phase the minimum of the nasal flow $F_{nasal}$ (bearing the reference number 84), and calculate the difference between this maximum and this minimum.

During a prolonged exhalation phase, that is to say one having for example a duration of greater than 3 seconds, the means 30 receive from the means 29 a control signal so as to calculate the amplitude of the nasal flow at each second, that is to say to calculate the difference between the nasal flow determined at a given instant and that at an instant preceding it by, for example, one second. In FIG. 3, this determination at closely-spaced intervals of time of the amplitude of the nasal flow is implemented by the means 30 onwards of the instant $t_1$.

II.2 Determination of an Obstructive Respiratory Event Termed "Limiting Rate of Flow"

Figure 4:
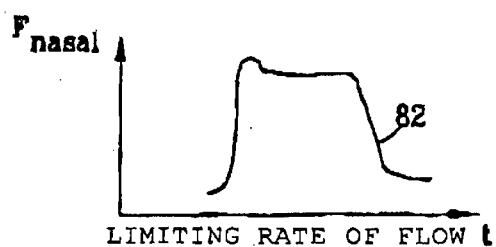
FIG. 4 represents a graph showing a nasal flow as a function of time in the case where the user's respiratory passages are impaired by partial obstruction.

A normal breathing cycle possesses a sinusoidal shape as represented in FIG. 3 up to the instant $t_0$. In the case of a partial obstruction of the user's respiratory passages, the inhalatory flow which increases at the start of an inhalation phase, is rapidly limited so that the curved $F_{nasal}$ possesses a clipped form. Such a curve 82 of $F_{nasal}$ as a function of time in the case of a limiting rate of flow is represented by way of example in the graph of FIG. 4.

Figure 5:
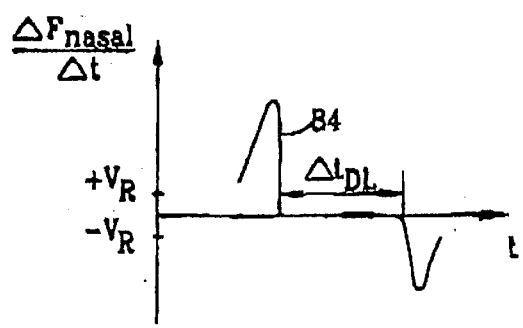
FIG. 5 represents a graph showing the time derivative of the nasal flow of FIG. 4.

In order to be able to detect such phenomenon accurately, the means 31 calculate, during an inhalation phase, the time derivative of the amplitude of the nasal flow $F_{nasal}$, represented by the curve 84 of FIG. 5.

The absolute value of the time derivative thus calculated is compared at each instant by the means 35 with a reference value $V_R$ recorded in the memory 37. Of course, it is also possible to make provision for several reference values if this proves necessary.

Furthermore, controlled by the comparison means 35, the means 39 measure the duration $\Delta t_{DL}$ for which the absolute value of the derivative is less than the reference value $V_R$.

Additionally, during $\Delta t_{DL}$ the means 41 chart the number of changes of sign of the derivative.

From the moment that $\Delta t_{DL}$ is greater than a threshold duration lying for example between one and two seconds, it is possible to conclude that the user is suffering from a partial obstructive phenomenon. This diagnosis is reinforced when the sign of the derivative changes many times during $\Delta t_{DL}$.

II.3 Determination of the Amplitude of the Buccal Flow of the User

The determination of the amplitude $A_{buccal}$ of the buccal flow $F_{buccal}$ by the means 42 for processing the signal delivered by the member 19 for qualitative measurement of the rate of flow, for example by measurement of the resistance of a thermistor, is similar to that of the amplitude $A_{nasal}$ for the nasal flow $F_{nasal}$. In effect, after some smoothing of the raw signal and the subtracting of an offset, the difference between the maximum and the minimum of the buccal flow $F_{buccal}$ is calculated.

Preferably, so as to reduce the calculation and processing steps, the amplitude $A_{buccal}$ is determined only during a phase of prolonged nasal exhalation, that is to say one having a duration of greater than 3 seconds. In this case, that is to say onwards of the instant $t_1$ represented in FIG. 3, the means 42 received from the means 29 a control signal so as to calculate the amplitude of the buccal flow at each second, that is to say to calculate the difference between the buccal flow determined at a given instant and that at an instant preceding it by, for example, one second.

II.4 Determination of a Phase of Snoring of the User

Figure 6:
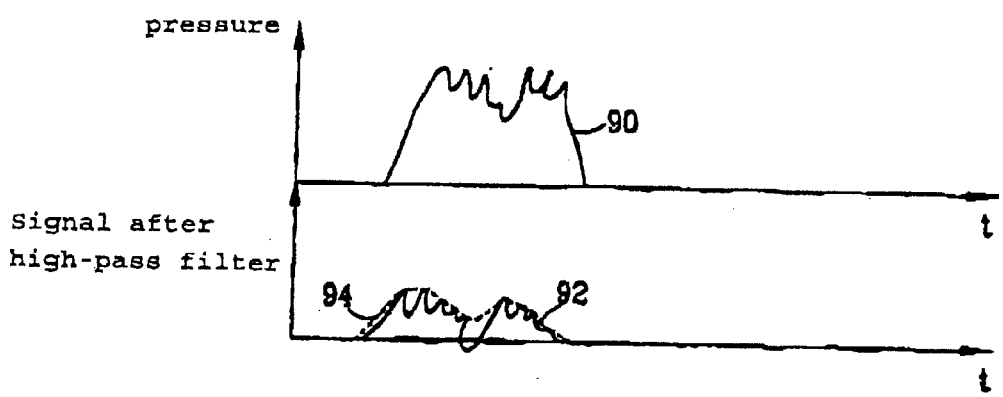
FIG. 6 shows two graphs to illustrate the determination of a snoring phenomenon from a pressure signal measured at the nose piece and/or mouthpiece applied to the user.

Snoring is characteristic of an obstructive phenomenon in the respiratory passages of a user. At the level of the pressure signal measured by the sensor 13, it is manifested by oscillations which are superimposed on the normal pressure signal as is represented in the upper graph of FIG. 6 showing by way of example a curve 90 representative of snoring.

To determine whether the user 3 is suffering from snoring, a high-pass filtering of the pressure signal is firstly carried out in the means 45 and the filtered signal is amplified in the means 47. The filtered and amplified signal is represented as a function of time by the curve 92 in the lower graph of FIG. 6.

Next, the amplified filtered signal is interpolated by way of the means 49 so as to obtain an envelope curve 94. This envelope curve 94 passes through all the maxima of the filtered and amplified signal and, in the case of snoring, exhibits a characteristic shape. This is why this envelope curve 94 is then compared in the means 53 with the reference curve recorded in the storage means 51 so as to determine the presence of snoring phases.

11.5 Conversion of the Processed Physical Variables into States of Fuzzy Variables with Degrees of Membership By way of example, explained in detail below is the conversion of a processed physical variable, the amplitude of the nasal flow $A_{nasal}$ when the duration of the nasal exhalation phase is greater than three seconds, so as to establish its degree of membership in one or more states of an associated fuzzy variable, called $A^f_{nasal}$ this conversion procedure is applied in a similar manner to all the other physical variables to be taken into account for applying rules according to fuzzy logic.

Figure 7:
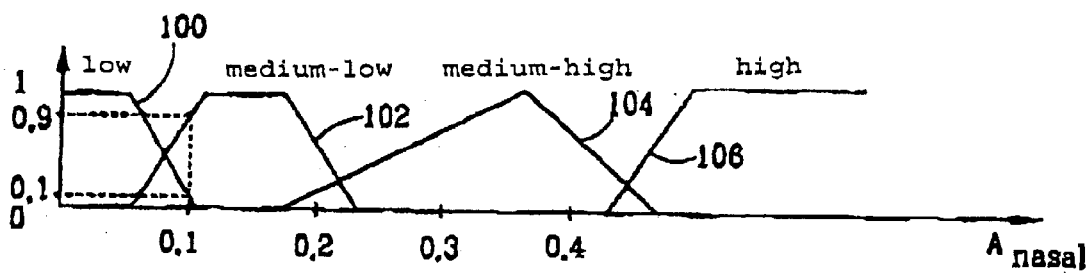
FIG. 7 shows a graph to illustrate the conversion of a measured physical variable with a view to establishing its degrees of membership in one or more states of a fuzzy variable.

Represented in FIG. 7 is a graph showing, along the abscissa, the universe of discourse of the nasal flow $A_{nasal}$ and, along the ordinate, the membership values of states of the associated fuzzy variable $A^f_{nasal}$.

As may be seen in the figure, the fuzzy variable $A^f_{nasal}$ can take four states, namely the states called "low", "medium-low", "medium-high" and "high".

With each state of $A^f_{nasal}$ there is associated a continuous curve 100, 102, 104 and 106 making it possible to establish the degree of membership of a value of $A_{nasal}$ in one or more states of the fuzzy variable $A^f_{nasal}$.

Thus for example, curve 100 is associated with the "low" state and exhibits the shape of a plateau following by a negative slope. Curve 102 is associated with the "medium-low" state and exhibits a trapezium shape. Curve 104 is associated with the "medium-high" state and exhibits a triangular shape, and curve 106 is associated with the "high" state and exhibits a positive slope followed by a plateau.

The shape of the curves 100, 102, 104 and 106 is defined empirically from clinical trials on users It is noted that the plateaus at the ends of the universe of discourse of the physical variables are generally retained.

Furthermore, the ordinate values of the curves 100, 102, 104 and 106 lie between zero (0) and one (1).

Moreover, it is important to note that the various curves 100, 102, 104 and 106 overlap in such a way that a value of $A_{nasal}$ can belong to two states of $A^f_{nasal}$.

Thus for example the value $A_{nasal}=0.1$ belongs to
- a "low" state of the fuzzy variable $A^f_{nasal}$ with a degree of membership of 0.1, and
- a "medium-low" state of the fuzzy variable $A^f_{nasal}$ with a degree of membership of 0.9.

This is also represented in FIG. 7.

These other physical variables are converted by the conversion means 55 according to the same principle.

II.6 Application of Rules to the States of Fuzzy Variables with Degrees of Membership The states together with their respective degrees of membership of the fuzzy variables are input into means 23 for applying rules stored in the memory 25 forming a knowledge base. These rules are defined empirically from clinical trials on users.

Each rule involves at least two different fuzzy variables to obtain for example a degree of membership in a state of a phase of sleep respiration of the user 3.

By way of example, indicated below is a suite of eleven rules for two fuzzy variables, the abovementioned fuzzy variable $A^f_{nasal}$ as well as the fuzzy variable $A^f_{buccal}$. This fuzzy variable $A^f_{buccal}$ can also take four states, namely the states referred to as "low", "medium-low", "medium-high" and "high", and the degrees of membership in these states are established from the amplitude of the buccal flow $A_{buccal}$ when the duration of the exhalation phase is greater than three seconds.

| No. | $A^f$buccal | $A^f$nasal | → | Phase of respiration |
|---|---|---|---|---|
| 1 | medium-high | medium-high | | normal |
| 2 | low | medium-high | | hypopnea |
| 3 | medium-low | medium-high | | hypopnea |
| 4 | medium-high | low | | hypopnea |
| 5 | low | low | | aphea |
| 6 | medium-low | low | | hypopnea |
| 7 | medium-high | medium-low | | hypopnea |
| 8 | low | medium-low | | hypopnea |
| 9 | medium low | medium-low | | hypopnea |
| 10 | high | | | normal |
| 11 | | high | | normal |

Let us assume that $A_{nasal}$ belongs to
- a "low" state of the fuzzy variable $A^f_{nasal}$ with a degree of membership of 0.1, and
- a "medium-low" state of the fuzzy variable $A^f_{nasal}$ with a degree of membership 0.9, and that $A_{buccal}$ belongs to
- a "low" state of the fuzzy variable $A^f_{buccal}$ with a degree of membership of 0.7, and
- a "medium-low" state of the fuzzy variable $A^f_{buccal}$ with a degree of membership 0.2.

The means 23 apply rules 1 to 11 in the following manner so as to determine the phases of respiration according to fuzzy logic.

Initially, the means 23 consider only the relevant rules, that is to say those rules for which a degree of membership is assigned to a state of the first fuzzy variable and a degree of membership is assigned to a state of the second fuzzy variable. In the present example, these are rules No. 5, 6, 8 and 9.

Next, a "MIN-MAX" selection order is applied. This order consists in assigning, initially, to a respiratory phase, associated with a specified rule, a degree of membership equal to the minimum of the degrees of membership of the states of the fuzzy variables which are to be considered in respect of this specified rule.

In the present example, by applying for example rule No. 5, we find that the sleep of the user 3 is in an "apnea" respiratory phase with a degree of membership equal to MIN (0.7; 0.1)=0.1.

Similarly, by applying rule No. 6 we find that the sleep of the user 3 is in a "hypopnea" respiratory phase with a degree of membership equal to MIN (0.2; 0.1)=0.1, by applying rule No. 8, in a "hypopnea" respiratory phase with a degree of membership equal to MIN (0.7; 0.9)=0.7, and by applying rule No. 9, in a "hypopnea" respiratory phase with a degree of membership equal to MIN (0.2; 0.9)=0.2.

As final result of the degrees of membership of the respective states of the respiratory phases of the sleep of the user according to fuzzy logic, consideration is subsequently given to the maximum membership value obtained for each state, namely in the present example 0 for the state of normal respiration, 0.1 for the state of apnea respiration and 0.7 for the state of hypopnea respiration.

Thus, it is understood that the use of fuzzy logic makes it possible to refine the diagnosis of the respiratory phases of a user.

Advantageously, the processing and conversion means 21 as well as the means 23 for applying rules and the memory 25 are embodied mainly through a computer comprising interfaces adapted for capturing the signals from the sensors 13, 17 and 19 and loaded with programs adapted for processing and utilizing these signals.

What is claimed is:

1. A process for determining respiratory phases of the sleep of a user, comprising:
   measuring at least two physical variables of which at least a first physical variable is representative of the nasal flow of the user, and of which at least a second physical variable is representative of the user's buccal flow;
   processing and converting each physical variable with a view to establishing its degree of membership in at least one state of a fuzzy variable; and
   applying pre-established rules between at least one state of a first fuzzy variable and a state of a second fuzzy variable so as to evaluate the degree of membership in a respiratory phase state of the sleep of the user according to fuzzy logic.

2. The process according to claim 1, wherein the respiratory state comprises at least one of a state of normal respiration, a state of apnea and a state of hypopnea.

3. The process according to claim 1, wherein each fuzzy variable possesses at least two states.

4. The process according to claim 1, wherein the degrees of membership of the states associated with a fuzzy variable are established on the basis of continuous curves defined over the entire universe of discourse of a measured physical variable.

5. The processing according to claim 1, wherein one of the measured physical variables is a pressure signal measured by a pressure sensor linked to a nose piece worn by the user.

6. The process according to claim 5, further comprising, during the step of processing and converting, extracting from the measured pressure signal snoring phases associated with breathing-obstruction phenomena.

7. The process according to claim 6, further comprising high-pass filtering of the pressure signal during extraction to obtain a filtered signal; amplifying the filtered signal to obtain an amplified filtered signal; interpolating the amplified filtered signal so as to obtain an envelope curve; and comparing the envelope curve with the reference curve so as to determine the presence of snoring phases.

8. The process according to claim 1, further comprising measuring the current consumed by a low-inertia turbine linked to a nose piece intended to be worn by the user to obtain an image of the nasal flow of the user.

9. The process according to claim 8, further comprising determining the phases of nasal inhalation and exhalation of the user during extraction; calculating the time derivative of the amplitude of the nasal flow during an inhalation phase; and utilizing the derivative so as to determine whether the user is or is not suffering from a partial obstructive phenomenon.

10. The process according to claim 9, wherein the step of utilizing the derivative of the amplitude of the nasal flow comprises comparing the absolute value of the derivative with at least one reference value, and measuring the duration for which the absolute value of the derivative is less than said at least one reference value.

11. The process according to claim 10, wherein the step of utilizing the derivative comprises charting the number of charges of sign of the derivative when the latter is less than the reference value.

12. The process according to claim 1, further comprising measuring the resistance of a thermistor placed in proximity to the mouth of the user to obtain an image of the buccal flow of the user.

13. Method for diagnosing the respiratory phases of the sleep of a patient suffering from respiratory sleep disorders, wherein said respiratory phases are determined according to the process according to claim 1.

14. Method for diagnosing according to claim 13, wherein the respiratory sleep disorder is sleep apnea or hypopnea.

* * * * *